United States Patent [19]
Lall et al.

[11] Patent Number: 5,962,733
[45] Date of Patent: Oct. 5, 1999

[54] GLUTAMINE CONTAINING ELECTROLYTE SOLUTION FOR CALF SCOURS

[75] Inventors: Rajiv Lall, Menomonie, Wis.; Daniel J. DuBordieu, Limerick, Me.

[73] Assignee: Vets Plus, Inc., Knapp, Wis.

[21] Appl. No.: 08/937,678

[22] Filed: Sep. 25, 1997

Related U.S. Application Data

[60] Provisional application No. 60/026,712, Sep. 25, 1996.

[51] Int. Cl.$^6$ .................................................. C07C 229/00
[52] U.S. Cl. ................................................ 562/563; 514/2
[58] Field of Search .................................. 514/2; 562/563

[56] References Cited

U.S. PATENT DOCUMENTS

| | | | |
|---|---|---|---|
| 3,898,328 | 8/1975 | Beigler | 424/128 |
| 4,164,568 | 8/1979 | Bywater | 424/153 |
| 5,300,629 | 4/1994 | Casteels | 530/326 |
| 5,317,084 | 5/1994 | Tomita | 530/324 |
| 5,338,724 | 8/1994 | Gabay | 514/12 |
| 5,447,914 | 9/1995 | Travis | 514/16 |
| 5,466,671 | 11/1995 | Tempst | 514/13 |
| 5,627,156 | 5/1997 | Talmadge | 514/13 |

OTHER PUBLICATIONS

Hamm, V.M.S.A.C 70, 279, 1975.
Barragry, Irish Veterinary Journal 28, 176–182, 1974.
Rhoad, Am. J. Physiol. 259, G 99–G 107, 1990.
Rhoad, Gastroenterology 100, 683–691, 1991.

*Primary Examiner*—Cecilia J. Tsang
*Assistant Examiner*—David Lukton
*Attorney, Agent, or Firm*—DeWitt Ross & Stevens S.C.

[57] ABSTRACT

Electrolytes and glucose are supplemented with 30 mmol/L glutamine to treat scours. This is administered to calves that experience watery, soft or foamy feces from various enteric diseases.

3 Claims, No Drawings

GLUTAMINE CONTAINING ELECTROLYTE SOLUTION FOR CALF SCOURS

CROSS REFERENCE TO RELATED APPLICATION

This application claims priority under 35 USC §119(e) to U.S. Provisional Patent Application Ser. No. 60/026,712 which was filed on Sep. 25, 1996, the entirety of which is incorporated by reference herein.

BIBLIOGRAPHIC CITATIONS

Full bibliographies of the references cited can be found at the end of the specification of this patent application.

FIELD OF THE INVENTION

This invention relates to methods of treating scours by administration of therapeutic levels of electrolytes and specifically an electrolyte solution containing glutamine.

DESCRIPTION OF RELATED ART

Scours is a major cause of death in newborn calves. Calves are at highest risk during the first week of life gradually dropping after four weeks (Frank and Kaneene, 1993). Calves that do not die from scours may be faced with a negative energy balance resulting in fat and carbohydrate malabsorption (Youanes and Herdt, 1987). Damage to intestinal epithelium with subsequent villous atrophy is assumed to be the mechanism responsible for malabsorption. Surviving calves will produce a lower lifetime milk yield and tend to be culled at a younger age than healthy cows (Skrzypek, 1990).

Scours is caused by a number of infectious agents including bacteria, such as *Escherichia coli* (*E. coli*) K99 and *Salmonella* species, viruses, such as Rotavirus, Coronavirus and Torovirus, and other pathogens such as Cryptosporidium species (Moerman, et al., 1986; Reynold, et al., 1986; WHO Scientific Working Group, 1980; Snodgrass, et al., 1986; Zschoeck, et al., 1987; Koopmans, et al., 1991). The metabolic change resulting from etiologic organisms causing scours are similar. They include: 1) dehydration, 2) acidosis, 3) electrolyte abnormalities and 4) negative energy balance and or hypoglycemia.

Disease symptoms are specific in Calves less than two 2 weeks old. They include watery feces, a fever of 103 to 105° F., dehydration due to fluid loss, depression and decreased appetite (Rebhun, 1984). Scours can spread through fecal/oral transmission. Because of the young age of these calves, dehydration, electrolyte losses, and acidosis may result in death in the most severe cases.

Water loss is an important aspect in scours. It is necessary to replace water in the scouring calf. Water is a principal component in bovine body tissues. The water content of adult cows ranges from 70 to 75% of the fat-free body weight (Kasari, 1994). However, immature animals tend to have even more body water with up to 86% body mass. The major cause of dehydration of scouring calves is fecal fluid loss, which can be as much as 13% of the body weight in 24 hours. Depletion of body water and electrolytes, in calf scours, usually occurs simultaneously, but the relative amount of water and electrolytes is not always constant. It is essential to supply electrolytes, particularly sodium, in addition to water for rehydration and volume replacement. Replacement of electrolytes can occur by intravenous or oral administration of solutions.

Endogenous factors that regulate fluid and electrolyte secretion include a variety of peptide hormones, neurotransmitters and products of immunologic effector cells. The exact mechanism by which scours occurs is dependent on the causative agent. Bacterial toxins are among the major exogenous factors that affect fluid and electrolyte secretion. Colibacillosis is one form of scours in calves that is caused by *E. coli* (House, 1978). *E. coli* must first be able to adhere to the calf intestinal mucosa and elaborate a heat sensitive enterotoxin, called STa (DeLopex, et al., 1982). STa is released into the lumen of the intestine, and subsequently excessive salt and water secretion occurs (*Pharmacol Rev.*, 1987; *J. Clin. Invest.*, 1988), resulting in scours. These effects are mediated by the activation of specific STa receptors in intestinal epithelial cell membranes. STa receptors are members of the guanylyl cyclase family (*J. Biol. Chem.*, 1991). STa receptor binding leads to increases in intestinal cell 5'-cyclic guanosine monophosphate (cGMP) concentrations. cGMP increase also leads to inhibition of neutral $Na^+$, $Cl^-$ absorption (Kaunitz, et al., 1995). Water subsequently leaves the intestinal cells via osmotic mechanisms and is expelled from the body, along with the lost electrolytes, in the form of watery feces.

Viral pathogens can mechanistically differ somewhat from enterotoxigenic induced scours where $Cl^-$ is actively secreted but mucosal surface area and $Na^+$—couple organic solute transport is preserved. Viral pathogens can impair glucose and amino acid couple $Na^+$ transport (McClung, et al., 1976; Rhoads, et al., 1986) along with defective NaCl absorption (MacLeod, et al., 1987), diminished disaccharide hydrolysis (Ferguson, et al., 1981; Keljo, et al., 1985; Kelly, et al., 1972) and reduced mucosal absorptive surface (McClung, et al., 1976; Kelly, et al., 1972).

The transport of water and the electrolytes $Na^+$, $K^+$, $Cl^-$, and $HCO3^-$ is a key function of the intestinal tract. Water molecules are moved in and out of the lumen by passive osmotic process. However, electrolytes are transported by an active process. Transcellular pathways that are involved in electrolyte transport consist of pumps, carriers and ion channels. Functional polarity of the intestinal epithelial cells occurs by having the location of the pumps, carriers and channels only in certain locations of the cell, thereby driving this transcellular movement of electrolytes through the cell.

$Na^+$ is the primary ion that drives water absorption in the intestine. In the small intestine, the co-transport of $Na^+$ with food—derived products and the electroneutral $Na^+$, $Cl^-$ absorptive mechanisms are responsible for most of the water and electrolyte absorption. The large intestine absorbs $Na^+$ through both electrogenic mechanisms involving apical $Na^+$ channels and an electroneutral $Na^+$, $Cl^-$ absorptive mechanism.

It is suggested (Kaunitz, et al., 1995) that electroneutral NaCl co-transport in the intestine results from a dual exchange system composed of a $Na^+/H^+$ ATPase is present on the apical membrane. To preserve intracellular ionic homeostasis, the following two transport mechanisms have been postulated: an apical, electroneutral $Cl^-/HCO3^-$ exchanger, which would preserve intracellular pH; and a basolateral $K^+$, $Cl^-$ cotransporter, which would account for the observed neutral transcellular movement of $K^+$.

$Na^+$-glucose co-transport and actively absorbing glucose are a major means by which the small intestine absorbs $Na^+$. A $Na^+$-glucose co-transport carrier on the apical membrane serves to bring glucose and $Na^+$ into the cell. $Na^+$ is then pumped out via the $Na^+$, $K^+$-ATPase pathway found on the basolateral membrane. Glucose proceeds across the basolateral membrane via a specific facilitated transport carrier. Similar $Na^+$ co-transport mechanisms exist for many amino acids.

With some of the mechanisms of sodium absorption in intestines being elucidated, new concepts for treating scours can emerge. A new pharmacological therapy concept for the treatment of scours should include the goal of stimulating neutral NaCl absorptive processes. Neutral NaCl absorptive mechanisms remain intact despite villus atrophy in at least cryptosporidia (Argenzio, et al., 1994) and rotavirus (Rhoads, et al., 1991) infection in the neonatal piglet model. Other mammals also have the capacity for neutral NaCl absorptive processes.

The addition of the amino acid L-glutamine to orally administer electrolytes should help achieve neutral NaCl Absorption and subsequent rehydration in scouring calves and other mammals. It has been shown that L-glutamine stimulates electrogenic $Na^+$ absorption (probably via $Na^+$/glutamine co-transport) as well as neutral NaCl absorption in neonatal piglet ileum models (perhaps mediated by a prostaglandin-sensitive apical $Na^+/H^+$ exchange) (Rhoads, et al., 1990; Rhoads, et al., 1991; Rhoads, et al., 1992; Argenzio, et al., 1994). Other animal models have also shown glutamine stimulated $Na^+$ absorption in rabbit ileum (Dechelotte, et al., 1989; Am J Physiol, 1992; Lima, et al., 1992).

L-glutamine is the principle circulating amino acid, accounting for around 50% of the total exchangeable amino acid pool (Souba, et al., 1985). Glutamine appears to be the major energy source for intestinal epithelium (Windmuellar, 1982). In addition, glutamine oxidation is increased in the bowel of newborn animals compared to adult animals (Kimura, 1987). Metabolism of glutamine to alpha-ketoglutarate and subsequent complete oxidation via the Kreb's cycle yields 30 moles of ATP per mole of glutamine. Also it has been demonstrated (Gardemann, et al., 1992) that luminal (or enteral) administration of glutamine enhances glucose absorption; however, this effect was not observed when glutamine was administered intravenously.

In animals, the intentional lowering of blood glutamine levels via an infusion of glutaminase results in watery feces, milk villus atrophy, mucosal ulceration's and intestinal necrosis (Bakerville, et al., 1980). The addition of glutamine to orally administered electrolytes will provide needed energy and other benefits, in addition to sodium absorption and subsequent water uptake to the intestine of souring calves and other mammals.

SUMMARY OF THE INVENTION

The invention provides administration of electrolytes and glucose with glutamine primarily to, but not limited to, calves exhibiting scours. It has been found that glutamine is effective in stimulating intestinal sodium absorption. Administration of electrolytes with glutamine should provide water absorption in calves and other mammals.

The invention is directed to a method for treating calf scours, which comprises orally administrating to the calf electrolytes containing glucose supplemented with glutamine or a glutamine analog or perhaps polypeptide of glutamine. A preferred administration is at 30 mmol glutamine per liter of electrolyte given.

The advantages of oral administration of solutions (oral solutions) compared to intravenous solutions are that oral solutions can be carried and stored in dry form. It is then mixed with tap water and administered by a nursing bottle or stomach tube as infrequently as every twelve hours. Thus, economy of time, materials, and equipment is achieved when compared to intravenous administration.

Oral solutions contain substantial amounts of sodium, chloride, potassium, and glucose. Most contain bicarbonate or other alkalinizing agents. Many contain glycine, acetate or citrate to enhance sodium and water absorption. Others contain calcium, magnesium, and phosphorus. The major differences between formulations occur in the concentration of glucose, alkalinizing agents and total osmolarity. These differences allow the veterinarian to choose the type that will work best in a particular given situation, as the etiology of scours is not the same in all cases. High energy solutions approach the maintenance need of the calf and reduce weight loss compared to oral solutions with less amounts of glucose.

Whenever acidosis is moderate to severe, oral solutions with alkalinizing agents must be used to restore normal acid-base status in a timely manner. Nonalkalinizing solutions are indicated for calves that have had fluid therapy instituted early in the course of the disease before dehydration or acidosis becomes severe.

DETAILED DESCRIPTION OF INVENTION

Glutamine Administration: The glutamine supplied to calves in this invention may include analogs, derivatives, substitution products, isomers, or homologs which retain the characteristics of glutamine. Administration is achieved by nursing bottle or by stomach tube in liquid form.

The composition of the electrolytes, glucose and glutamine may vary to include other electrolytes and concentrations. Various forms of scours may or may not require the presence of alkalinizing agents such as bicarbonate. A typical formulation consists of 100 mEq/L of $Na^+$, 15 mEq/L of $K^+$, 70 mEq/L of Cl, 80 mEq/L $HCO3^-$, 75 g/L of glucose, 30 mmol/L of glutamine.

While this invention may be embodied in many forms, it is described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claim attached hereto.

BIBLIOGRAPHY

Am J. Physiol 1992; 262: G312–G310.
Pharmacol Rev. 1987, 39: 163–169
J Clin Invest. 1988, 82: 512–523
J Biol Chem, 1991 266: 17912–17918.
Argenzio R A, Rhosads M J, Armstrong M. and Gomez G. "Glutamine stimulates prostaglandin-sensitive $Na^+$—$H^-$ exchange in experimental porcine cryptosporidiosis." Gastroenterology 106: 1418–1428 1994.
Bakerville A, Hambleton P, Benbough J E. "Pathologic features of glutaminase toxicity." Bra J Exp Path. 1980; 61: 132–138.
Chao A C, de Sauvvage F J, Dong Y J, Wagner J A, Goeddel D V, and Gardner P.; "STa receptors: Physiological and pathphysiolocial regulation of intestinal secretion by 5"-cyclic guanosine monophosphate," Gastroenterology 109: 325–327 1995.
Dechelotte P, Darmaun D. Rongier M and Desjeux J F. "Glutamine Transport in isolated rabbit ileal epithelium." Gastroentrol Clin Biol. 1989; 13: 816–821.
DeLopex A G, Kadis S, Shotts E B. "Enterotoxin production and resistance to antimicrobial agents in porcine and bovine." Escherichia coli strains." Am J Vet Res. 1982; 43: 1286–1287.

Ferguson A, Paul G, Snodgrass D R. "Lactose tolerance in lambs with rotavirus diarrhea." *Gut* 1981; 22: 114–119.

Frank N A and Kaneene J B "Management risk factors associated with calf diarrhea in Michigan dairy herds." *J. Dairy Sci.* 76: 1313–1323 1993.

Gardemann A, Watanabe Y, Grobe V, Hesse S. Jungermann K. Increase in intestinal glucose absorption and hepatic glucose uptake elicited by luminal but not vascular glutamine in the jointly perfused small intestine and liver of the rat." *Biochem J* 1992; 283: 759–765.

Kasari R. "Medical management of common physiologic and metabolic abnormalities in anorectic cattle." *Veterinary Medicine* Sept. 1994; p. 898–909.

Kaunitz J D, Barrett K E and McRoberts J A. "Electrolyte secretion and absorption: small intestine and colon" from *Textbook of Gastroenterology* edited by Yamada T. JB Lippincourt Co., Philadelphia 1995.

Keljo D j, MacLeod R J, Perdue M H, Butler D G, Hamilton J R. D-glucose transports in piglet jejunal brush-border membranes: insights from a disease model." *Am J. Physiology.* 259: G99–G107. 1990.

Kelly M, Butler D G, Hamilton J R. "Transmissible gastroenteritis of piglets: a model of infantile viral diarrhea." *J. Pediatr.* 1972; 80: 925–931.

Kimura R E. "Glutamine oxidation by developing rat small intestine." *Pediatr. Res.* 21: 214–217 1987.

Koopmans M, van Wuijckhuise L, Schukken Y H, et al. Association of diarrhea in cattle with Rotavirus infection on farms." *Am J Vet. Res.* 1991: 52: 1769–1773.

Lima A A, Soares A M Freire-Junior J E, Guerrant R L. "Cotransport of sodium with glutamine, alanine and glucose in the isolated rabbit ileal mucosa." *Braz J Med. Biol. Res.* 1992; 25: 637–640.

MacLeod R J, Hamilton J R. "Absence of cAMP-mediated antiabsorptive effect in an undifferentiated jejunal epithelium. *Am J. Physiol.* 1987; 252: G776–782.

McClung H J, Butler D G, Kerzner B, Gall D G, Hamilton J R. "Mucosal ion transport in acute viral enteritis." *Gastroenterology* 1976: 70: 1091–1095

Moerman, A, van Zijderveld F G, de Lieuw P W et al. "Neonatal calf diarrhea." *Ann Rep Central Vet Institute, Lelystad* 1986; 36–41.

Rebhun, W C "Digestive disease." In 1984 Year Book of Agriculture. *Animal Health Livestock and Pets.* Jack Hayes editor. US government publication LC 84-601135.

Reynold D J, Morgan J H, Chanter N, et al., "Microbiology of calf diarrhea in Southern Britain." *Vet Rec.* 1986; 119: 34–39.

Rhoad M J, Keko E O, Woodard J P et al. "L-glutamine with D-glucose stimulate oxidative metabolism and NaCl absorption in piglet jejunum." *Am J. Physiol.* 236: g960–g966, 1992.

Rhoad M J, Keku E O, Bennett L E, Quin J, and Lecce J G. "Development of L-glutamine-stimulated electroneutral sodium absorption in piglet jejunum. "*Am. J. Physiology.* 259: g99–G107.

Rhoad M J, Keko E O, Quin J et al. "L-glutamine stimulate jejunal sodium and chloride absorption in pig rotavirus enteritis." *Gastroenterology* 100: 683–691, 1991.

Rhoads J M, MacLeod R J, Hamilton J R. "Alanine enhances jejunal sodium absorption in the presence of glucose: studies in piglet viral diarrhea." *Pediatr. Res.* 1986; 20: 879–883.

Skrzypek R. "The consequent effects of diarrhea in calves on blood composition and performance." *American Diary Science Association JDS* Vol. 73 Suppi. 1. 1990 p 296.

Snodgrass D R, Terzolo H R, Sherwood D, et al. "Aetiology of diarrhea in young calves." *Vet Rec.* 1986; 119: 31–43.

Souba, W. W., Smith R. J., and Wilmore, D. W. "Glutamine metabolism by the intestinal tract." *J. Parenter. Enteral. Nutr.* 9: 608–617, 1985.

WHO Scientific Working Group. "Rotavirus and other viral diarrheas." *Bull. WHO* 1980; 58: 183–198.

Windmueller H G. "Glutamine utilization by the small intestine." *Adv. Enzymology* 53: 202–231, 1982.

Youanes Y D and Herdt T H. "Changes in small intestinal morphology and flora associated with decreased energy digestibility in calves with naturally occurring diarrhea. " *Am J Vet Res.* 48: 719–725 1987.

Zschoeck M, Herbst W, Hamann H P, et al., "Electronenmikroskopishe un bakteriologische Untersuchungsergebnisse bei der Diarrhoe der Kaelber. " *Prakt Tierarzt.* 1987; 8: 5–9.

We claim:

1. A method for enhancing sodium and water uptake in scouring calves comprising administering to the calves therapeutically effective amounts of electrolytes and glucose supplemented with glutamine.

2. The method of claim 1 wherein the glutamine is administered at a concentration of from 5 to 90 mmol glutamine per liter of electrolyte.

3. A method for enhancing sodium and water uptake in a scouring calf comprising administering thereto therapeutically effective amounts of electrolytes and glucose supplemented with a glutamine analog, a polypeptide consisting of glutamine residues, or a mixture of the glutamine analog and said polypeptide;

wherein said glutamine analog is an amino acid which is a derivative, isomer or homolog of glutamine that retains a side-chain carboxamide moiety.

* * * * *